(12) United States Patent
Embrey et al.

(10) Patent No.: US 7,756,585 B2
(45) Date of Patent: Jul. 13, 2010

(54) MUSCLE STIMULATION METHOD AND SYSTEM TO IMPROVE WALKING

(75) Inventors: David G. Embrey, Puyallup, WA (US); Samuel F. Augsburger, Nicholasville, KY (US)

(73) Assignee: Good Samaritan Children's Therapy Unit, Puyallup, WA (US)

( * ) Notice: Subject to any disclaimer, the term of this patent is extended or adjusted under 35 U.S.C. 154(b) by 584 days.

(21) Appl. No.: 11/342,589

(22) Filed: Jan. 31, 2006

(65) Prior Publication Data

US 2007/0179561 A1    Aug. 2, 2007

(51) Int. Cl.
*A61N 1/18* (2006.01)

(52) U.S. Cl. .......................................... 607/49
(58) Field of Classification Search .............. 607/46, 607/48, 49
See application file for complete search history.

(56) References Cited

U.S. PATENT DOCUMENTS

| | | | |
|---|---|---|---|
| 3,083,712 A | 4/1963 | Keegan, Jr. | |
| 3,881,496 A * | 5/1975 | Vredenbregt et al. | 607/49 |
| 4,005,296 A | 1/1977 | Olson | |
| 4,697,808 A | 10/1987 | Larson et al. | |
| 5,014,705 A | 5/1991 | Graupe et al. | |
| 5,167,229 A | 12/1992 | Peckham et al. | |
| 5,748,845 A | 5/1998 | Labun et al. | |
| 5,766,236 A | 6/1998 | Detty et al. | |
| 5,776,171 A | 7/1998 | Peckham et al. | |
| 5,861,017 A | 1/1999 | Smith et al. | |
| 6,226,552 B1 | 5/2001 | Staunton et al. | |
| 6,456,884 B1 | 9/2002 | Kenney | |
| 6,507,757 B1 | 1/2003 | Swain et al. | |
| 6,652,443 B1 | 11/2003 | Struppler et al. | |
| 6,654,642 B2 | 11/2003 | North et al. | |
| 6,701,189 B2 | 3/2004 | Fang et al. | |
| 6,788,976 B2 | 9/2004 | Gesotti | |
| 2001/0000187 A1 | 4/2001 | Peckham et al. | |
| 2001/0000782 A1 | 5/2001 | Schiessl | |
| 2003/0139783 A1 | 7/2003 | Kilgore et al. | |
| 2003/0144710 A1 | 7/2003 | Haugland et al. | |
| 2003/0181956 A1 | 9/2003 | Duncan et al. | |
| 2004/0019369 A1 | 1/2004 | Duncan et al. | |

(Continued)

OTHER PUBLICATIONS

Damiano DL. Reviewing muscle co-contraction: Is it a developmental, pathological, or motor control issue? *Phys Occup Ther Ped.* 1993;12:3-21.

(Continued)

*Primary Examiner*—George R Evanisko
*Assistant Examiner*—Michael D'Abreu
(74) *Attorney, Agent, or Firm*—Birch, Stewart, Kolasch & Birch, LLP

(57) ABSTRACT

In a method and a system of providing walking assistance and/or therapy to a person with impaired gait, electrical stimulation is applied to muscles of a leg that effect dorsiflexion and plantar flexion of the ankle of the leg. The timing of the electrical stimulation is determined from gait event signals developed from sensors under the heel and forepart of the foot of the other leg. In the method and the system, the electrical stimulation is enabled when the person is sensed to be active and is disabled when the person is sensed to be inactive. The method and the system are applicable to persons having unilateral or bilateral impairment of their walking ability.

20 Claims, 3 Drawing Sheets

U.S. PATENT DOCUMENTS

| | | | |
|---|---|---|---|
| 2004/0082979 | A1 | 4/2004 | Tong et al. |
| 2004/0122483 | A1* | 6/2004 | Nathan et al. ............... 607/49 |
| 2004/0127954 | A1 | 7/2004 | McDonald, III |

OTHER PUBLICATIONS

Cowan MM, Stilling DS, Naumann S, Colborne GR. . Quantification of antagonist muscle co-activation in children with spastic diplegia. *Clin Anat* 1998;11(5):314-9.

Ikeda AJ, Abel MF, Granata KP, Damiano DL. Quantification of co-contraction in spastic cerebral palsy. *Elecrromyogr. Clin Neurophysiol.* 1998;38:497-504.

Unnithan VB, Dowling JJ, Frost G, Volpe Ayub B, Bar-Or O. Co-contraction and phasic activity during GAIT in children with cerebral palsy. *Electromyogr Clin Neurophysiol.* 1996;36:487-94.

Crenna P. Spasticity and 'spastic' gait in children with cerebral palsy. *Neurosci Biobehav Rev.* 1998;22(4):571-8.

Damiano DL, Vaughn CL, Abel MF. Muscle response to heavy resistance exercise in children with spastic cerebral palsy. *Dev Med Child Neruol.* 1995;37:731-739.

Damiano DL, Kelly LE, Vaughn CL. Effects of quadriceps femoris muscle strengthening on crouch gait in children with spastic diplegia. *Phys Ther.* 1995;75:658-667.

Kerr C, McDowell B, McDonough S. Electrical stimulation in cerebral palsy: a review of effects on strength and motor function. *Dev Med Child Neurol.* 2004;46(3):205-13.

Atwater SW, Tatrarka ME, Katherine JE. Electromyography-triggered electrical muscle stimulation for children with cerebral palsy: A pilot study. *Ped Phys Ther.* 1991;3:190-199.

Carmick J. Clinical use of neuromuscular electrical simulation for children with cerebral palsy, Part 1: Lower Extremity. *Phys Ther.* 1993;73:505-513.

Carmick J. Clinical use of neuromuscular electrical simulation for children with cerebral palsy, Part 2: Upper Extremity. *Phys Ther.* 1993;73:514-522.

Carmick J. Managing equinus in children with cerebral palsy with electrical simulation to strengthen the triceps surae muscle. *Dev Med Child Neuro.* 1995;37:965-975.

O'Keeffe DT, Lyons GM. A versatile drop foot stimulator for research applications. Med Eng Phys. Apr. 2002;24(3):237-42.

van der Aa HE, Bultstra G, Verloop AJ, Kenney L, Holsheimer J, Nene A, Hermens HJ, Zilvold G, Buschman HP. Application of a dual channel peroneal nerve stimulator in a patient with a "central" drop foot. *Acta Neurochir Suppl.* 2002;79:105-7.

Chen YL, Li YC, Kuo TS, Lai JS. The development of a closed-loop controlled functional electrical stimulation (FES) in gait training. J Med Eng Technol. Mar.-Apr. 2001;25(2):41-8.

Kido Thompson A, Stein RB. Short-term effects of functional electrical stimulation on motor-evoked potentials in ankle flexor and extensor muscles. *Exp Brain Res.* Jul. 9, 2004.

Taylor PN, Burridge JH, Dunkerley AL, Wood DE, Norton JA, Singleton C, Swain ID. Clinical use of the Odstock dropped foot stimulator: its effect on the speed and effort of walking. *Arch Phys Med Rehabil.* 1999;80(12):1577-83.

Brandell BR. Development of a universal control unit for functional electrical stimulation (FES). *Am J Phys Med.* 1982;61(6):279-301.

Pierce SR, Laughton CA, Smith BT, Orlin MN, Johnston TE, McCarthy JJ. Direct effect of percutaneous electrical stimulation during gait in children with hemiplegic cerebral palsy: a report of 2 cases. *Arch Phys Med Rehabil.* 2004;85(2):339-43.

Yan T, Hui-Chan CW, Li LS. Functional Electrical Stimulation Improves Motor Recovery of the Lower Extremity and Walking Ability of Subjects With First Acute Stroke. A Randomized Placebo-Controlled Trial. *Stroke.* 2005;36(1):80-5.

Burridge JH, McLellan, DL. Relation Between Abnormal Patterns of Muscle Activation and Response to Common Peroneal Nerve Stimulation in Hemiplegia. *Neurol Neurosurg Psychiatry.* 2000;69:353-361.

Dimitrijević MR, Faganel J, Sherwood AM, McKay WB. Activation of Paralysed Leg Flexors and Extensors During Gait in Patients After Stroke. *Scan J Rehab Med 13*, 1981; 13:109-115.

Kenney L, Bultstra G, Buschman R, Taylor P, Mann G, Hermens H, Holsheimer J, Nene A, Tenniglo M, van der Aa H, Hobby J. An Implantable Two Channel Drop Foot Stimulator: Initial Clinical Results. *Artificial Organs.* 2002;26(3):267-270.

Burridge J, Taylor P, Hagan S, Swain I. Experience of Clinical Use of the Odstock Dropped Foot Stimulator. *Artifical Organs.* 1997;21(3):254-260.

Burridge JH, Taylor PN, Hagan SA, Wood DE, Swain ID. The Effects of Common Peroneal Stimulation on the Effort and Speed of Walking: a Randomized Controlled Trial With Chronic Hemiplegic Patients. *ClinicalRehabilitation.* 1997;11:201-210.

Taylor PN, Burridge JH, Dunkerley AL, Lamb A, Wood DE, Norton JA, Swain ID. Patients' Perceptions of the Odstock Dropped Foot Stimulator (ODFS). *ClinicalRehabilitation.* 1999;13:439-446.

Hausdorff JM, Ladin Z, Wei JY. Footswitch System for Measurement of the Temporal Parameters of Gait. *J Biomechanics.* 1995;28(3):347-351.

Comeaux P, Patterson N, Rubin M, Meiner R. Effect of Neuromuscular Electrical Stimulation During Gait in Children With Cerebral Palsy. *Pediatric Physical Therapy.* 1997;9:103-109.

Bertoli DB, Stanger M, Betz RR, Akers J, Maynahon M, Mulcahey MJ. Percutaneous Intramuscular Functional Electrical Stimulation as an Intervention Choice for Children With Cerebral Palsy. *Pediatric Physical Therapy.* 1997;9:123-127.

Hazlewood ME, Brown JK, Rowe PJ, Salter PM. The Use of Therapeutic Electrical Stimulation in the Treatment of Hemiplegic Cerebral Palsy. *Developmental Medicine and Children Neurology.* 1994;36:661-673.

Pierce SR, Orlin MN, Lauer RT, Johnston TE, Smith BT, McCarthy JJ. Comparison of Percutaneous and Surface Functional Electrical Stimulation During Gait in a Child With Hemiplegic Cerebral Palsy. *Am J Phys Med Rehabil.* 2004;83(10):798-805.

Johnston TE, Finson RL, McCarthy JJ, Smith BT, Betz, RR, Mulcahey MJ. Use of Functional Electrical Stimulation to Augment Traditional Orthopaedic Surgery in Children With Cerebral Palsy. *J Pediatr Orthop.* 2004:24(3):283-291.

Perry J, Garrett M, Gronley JK, Mulroy SJ. Classification of Walking in the Stroke Population. *Stroke.* 1995;26:982-989.

Ada L, Vattanasilp W, O'Dwyer NJ, Crosbie J. Does Spasticity Contribute to Walking Dysfunction After Stroke? *J Neurol Neurosurg Psychiatry.* 1998;64:628-635.

Smith BT, Coiro DJ, Finson R, Betz RR, McCarthy J. Evaluation of Force-Sensing Resistors for Gait Event Detection to Trigger Electrical Stimulation to Improve Walking in the Child With Cerebral Palsy. *IEEE Transactions on Neural Systems and Rehabilitation Engineering.* 2002;10(1):22-29.

Glanz M, Klawansky S, Stason W, Berkey C, Chalmers, TC. Functional Electrostimulation in Poststroke Rehabilitation: A Meta-Analysis of the Randomized Controlled Trials. *Arch Phys Rehabil.* 1996; 77:549-553.

\* cited by examiner

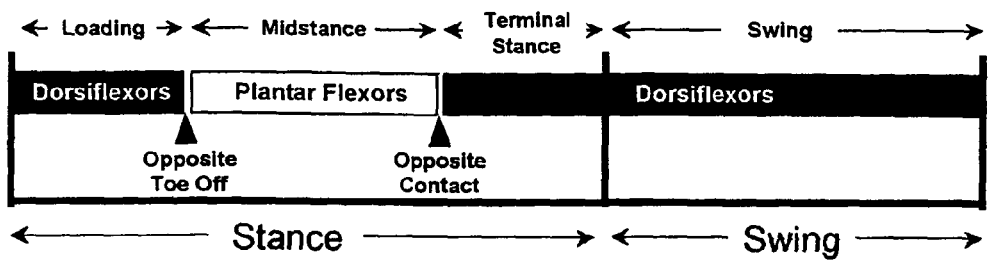
FIG. 3
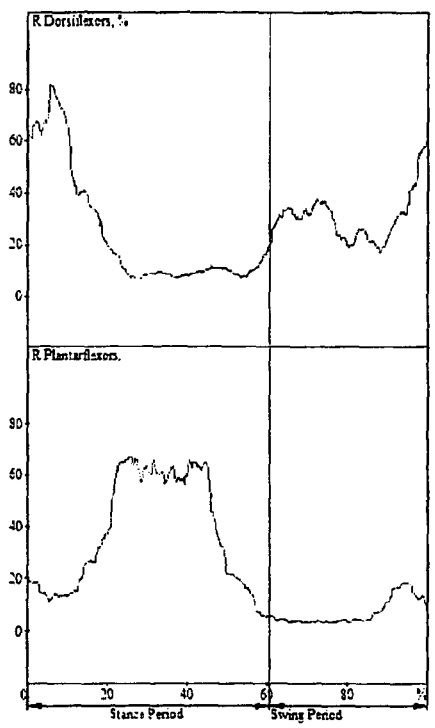
FIG. 4A
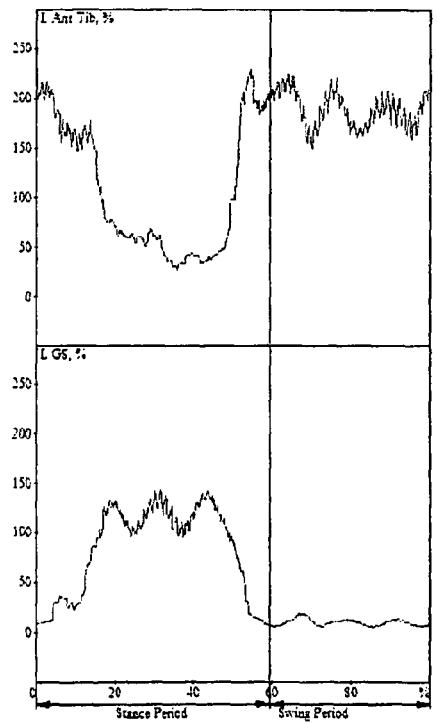
FIG. 4B

MUSCLE STIMULATION METHOD AND SYSTEM TO IMPROVE WALKING

BACKGROUND OF THE INVENTION

1. Field of the Invention

The present invention relates generally to a method and a system for electrical stimulation of muscles to augment and improve muscle function. More particularly, the present invention relates to a method and a system for electrically stimulating muscles in the leg or legs of a person with impaired walking ability in order to effect improvement in the person's walking ability.

2. Description of Related Art

There are over four million adults with impairments due to stroke in the United States. An estimated 500,000 Americans have cerebral palsy and 6,000 babies are born each year in the United States with cerebral palsy. The inefficiency of walking significantly impairs the ability of individuals with stroke and cerebral palsy to maneuver in their homes, at work, and in recreation. Many other individuals have impaired walking skills due to spina bifida, muscular dystrophy, Parkinson's disease, multiple sclerosis, spinal cord injury, Downs' Syndrome, idiopathetic toe walking, and peripheral neuropathies. Electrical simulation applied to key leg muscles has shown promise for improving the walking abilities for individuals with these disorders.

The use of Functional Electrical Stimulation (FES), first called "Electrical Muscle Therapy," was disclosed in U.S. Pat. No. 3,083,712 issued in 1963 to James E. Keegan Jr. The Keegan, Jr. invention employed electrical muscle stimulation to lift the foot during the swing phase of walking by applying small electrical currents to the dorsiflexor muscles. In adults with stroke, a disability called "drop foot" is caused by the inability to lift the toes (dorsiflex) when stepping forward in the swing phase of walking. This problem could cause the people to trip, fall, or injure themselves. The Keegan, Jr. patent, while addressing the problem of diminished muscle function that results in foot drop, offers no disclosure of how the patented invention could be applied to other muscles that participate in walking.

Over the past four decades, drop foot stimulators have been shown to be beneficial. However, this method is limited because it applies FES only to the dorsiflexors. Because these devices treat just this one problem, they do not teach the patient new motor patterns. The effects only occur when the stimulation is applied, and the patient is not re-trained to learn other muscle recruitment patterns. Moreover, drop foot is just one component of the walking deficits of adults with stroke. For example, adults with stroke do not effectively push on each step with their plantar flexors. About eighty percent of the acceleration force necessary to maintain walking comes from the plantarflexors. Nevertheless, electrical stimulation to these muscles has received little attention.

SUMMARY OF THE INVENTION

According to one aspect of the present invention, there is provided a method of providing walking assistance and/or therapy to a person with impaired gait, the method comprising the steps of: developing first gait event signals in response to pressure sensed between the heel of the foot of one leg and a support surface while walking; developing second gait event signals in response to pressure sensed between the forepart of the foot of the one leg and the support surface while walking; applying electrical stimulation to at least one muscle in the other leg that effects dorsiflexion of the ankle of the other leg in response to at least one of the first and second gait event signals; and applying electrical stimulation to at least one muscle in the other leg that effects plantar flexion of the ankle of the other leg when both of the first and second gait event signals are absent.

The method may additionally include the steps of: developing an activity signal in response to sensed movement of the person; allowing the transmission of electrical stimulation to the muscles in response to the activity signal; and blocking the transmission of electrical stimulation to the muscles when the activity signal is absent.

According to another aspect of the present invention, there is provided a method of providing walking assistance and/or therapy to a person with impaired gait, the method comprising the steps of: developing first gait event signals in response to pressure sensed between the heel of the foot of each leg and a support surface while walking; developing second gait event signals in response to pressure sensed between the forepart of the foot of each leg and the support surface while walking; applying electrical stimulation to at least one muscle in each leg that effects dorsiflexion of the ankle of the leg in response to at least one of the first and second gait event signals derived from the other leg; and applying electrical stimulation to at least one muscle in each leg that effects plantar flexion of the ankle of the leg when both of the first and second gait event signals derived from the other leg are absent.

According to another aspect of the present invention, there is provided a system for providing walking assistance and/or therapy to a person with impaired gait, the system comprising: a first sensor for developing a first gait event signal in response to pressure sensed between the heel of the foot of one leg and a support surface while walking; a second sensor for developing a second gait event signal in response to pressure sensed between the forepart of the foot of the one leg and the support surface while walking; and at least one pair of first electrodes for applying electrical stimulation to at least one muscle in the other leg that effects dorsiflexion of the ankle of the other leg; at least one pair of second electrodes for applying electrical stimulation to at least one muscle in the other leg that effects plantar flexion of the ankle of the other leg; and an electrical stimulation device configured to receive the first and second gait event signals and provide an electrical stimulation output to the electrodes, the electrical stimulation device providing (1) an electrical stimulation output to the at least one pair of first electrodes in response to the reception of at least one of the first and second gait event signals and (2) an electrical stimulation output to the at least one pair of second electrodes when both of the first and second gait event signals are absent.

The system may additionally include a third sensor for developing an activity signal in response to sensed activity of the person; and a control device that (1) allows the transmission of electrical stimulation to the muscles in response to the activity signal and (2) blocks the transmission of electrical stimulation to the muscles when the activity signal is absent.

According to another aspect of the present invention, there is provided a system for providing walking assistance and/or therapy to a person with impaired gait, the system comprising: first sensors for developing first gait event signals in response to pressure sensed between the heel of the foot of each leg and a support surface while walking; second sensors for developing second gait event signals in response to pressure sensed between the forepart of the foot of each leg and the support surface while walking; at least one pair of first electrodes for each leg; at least one pair of second electrodes for each leg; and an electrical stimulation device configured to receive the first and second gait event signals derived from each leg and provide an electrical stimulation output to the electrodes, the electrical stimulation device providing (1) an electrical stimulation output to the at least one pair of first electrodes of one leg in response to the reception of at least one of the first and second gait event signals derived from the other leg and (2) an electrical stimulation output to the at least one pair of second electrodes of one leg when both of the first and second gait event signals derived from the other leg are absent.

BRIEF DESCRIPTION OF THE DRAWINGS

FIG. 3 is a graphical representation of a normal timing sequence for activation of the dorsiflexors and plantar flexors during walking;

FIG. 4A is a graphical representation of recorded surface electromyographic data for a person with normal walking skills;

FIG. 4B is a graphical representation of recorded surface electromyographic data for a person with unilaterally impaired walking skills using the method and system of the present invention; and FIG. 5 is a schematic illustration of the system of the present invention being used by a person with bilateral walking impairment.

DETAILED DESCRIPTION OF PREFERRED EMBODIMENTS

Figure 1:
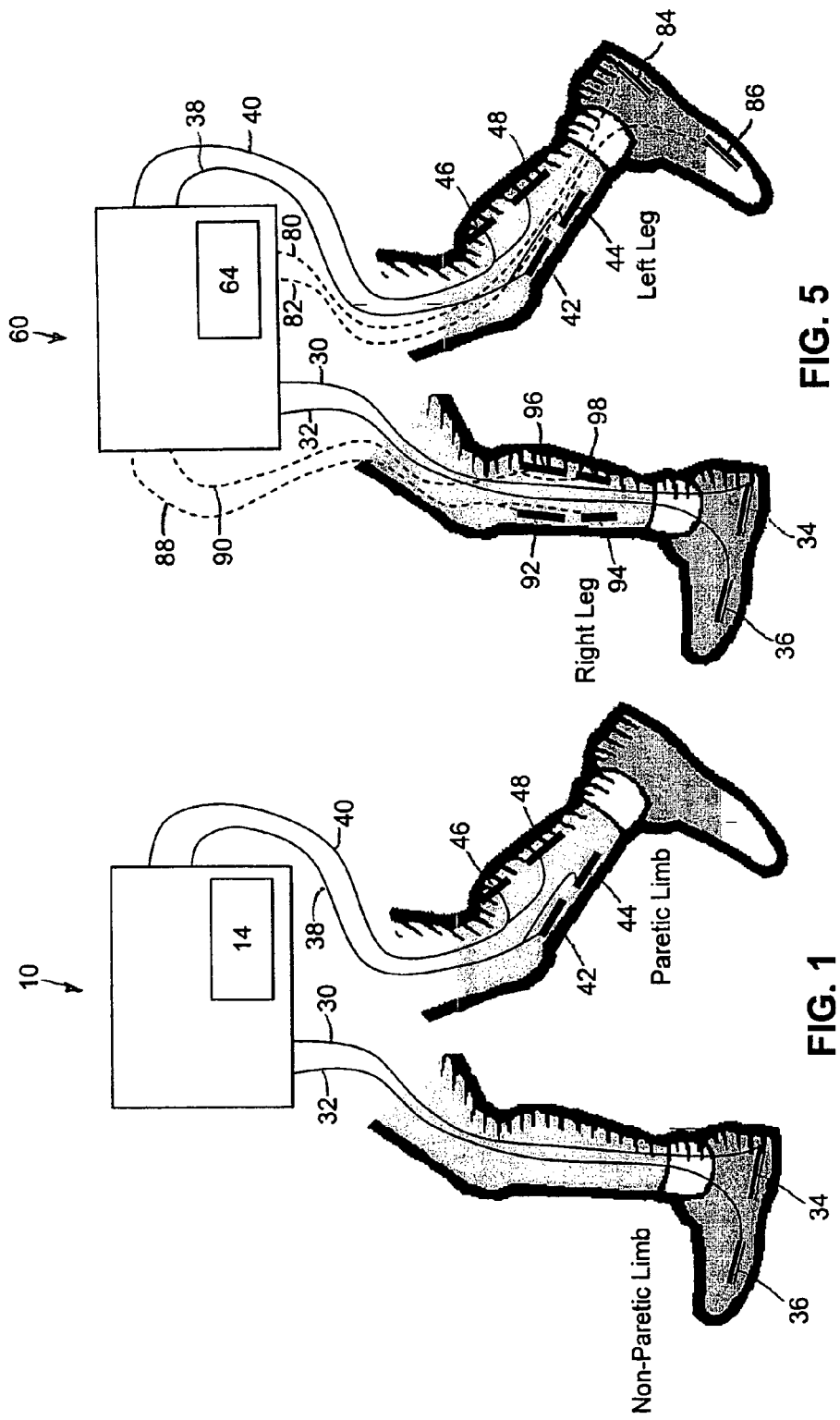
FIG. 1 is a schematic illustration of the system of the present invention being used by a person with unilateral walking impairment.

As shown schematically in FIG. 1, an individual using a unilateral embodiment of the system of the present invention carries a module 10 provided with input leads 30, 32 that conduct signals from switches 34, 36 placed under the heel and forepart, respectively, of the foot of the unimpaired leg (non-paretic limb). As shown, the switches are placed in a shoe worn by the individual. The switches employed may be well-known types that will close in response to pressure that occurs between the underside of the foot and a support surface as the individual walks. The module is provided with output leads 38, 40 that conduct electrical stimulation pulses from the module to pairs of electrodes 42, 44 and 46, 48 positioned to apply the stimulation pulses to at least two muscles of the impaired leg (paretic limb). The electrodes may be of known surface, needle or implanted types. As shown, the electrodes 42, 44 are positioned to stimulate a muscle (or muscles) that contracts in response to the electrical stimulation to effect dorsiflexion of the ankle. Based on the particular needs of the individual, these muscles may include the tibialis anterior, extensor hallicus longus, and extensor digitouum longus. Electrodes 46, 48 are positioned to stimulate a muscle (or muscles) that contracts in response to the electrical stimulation to effect plantar flexion of the ankle. These muscles may include the medial gastrocnemius, lateral gastrocnemius, soleus, peroneus longus, and tibialis posterior.

Figure 2:
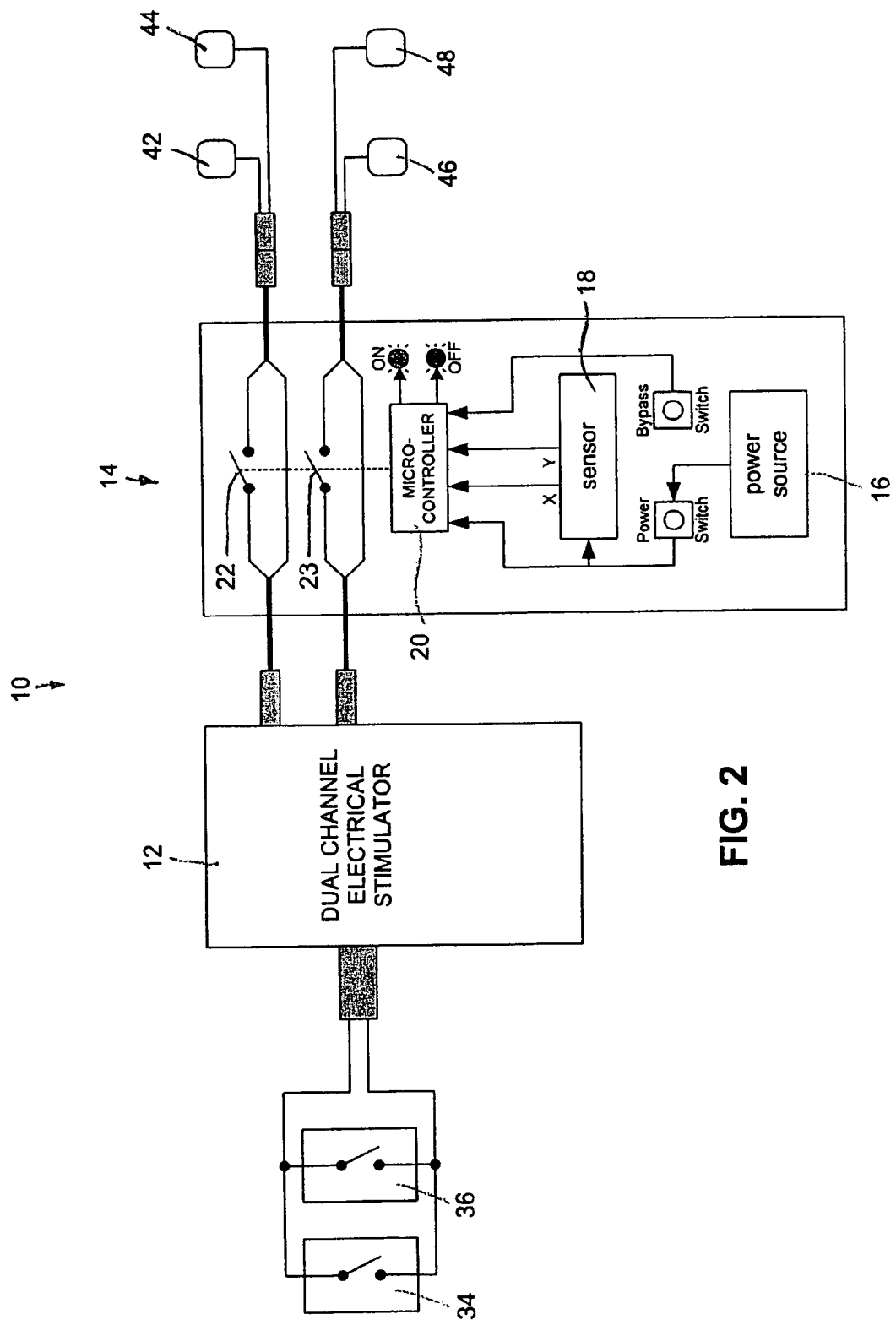
FIG. 2 is a schematic illustration of components employed in an embodiment of the system of the present invention for use by persons with unilateral walking impairment.

As illustrated schematically in FIGS. 1 and 2, the module 10 may incorporate a known electrical stimulation device 12 that delivers electrical stimulation in the form of low voltage output pulses on leads 38, 40 in response to input signals received on leads 30, 32 from the foot switches 34, 36. One of several known stimulation devices that will perform suitably for this application is a model 300 PV Neuromuscular Electrical Stimulation Device manufactured by Empi, Inc. of St. Paul, Minn., USA. As is known, the electrical stimulation device can be used to deliver electrical stimulation pulses on two output channels that are triggered by an external switch. When the switch is closed, one of the channels will be active, i.e., will deliver electrical stimulation pulses along an output lead. When the switch is open, the other of the two channels will be active, and electrical pulses will be delivered along another output lead.

Again referring to FIGS. 1 and 2, a the foot switches 34, 36 are arranged in parallel so that closing either of the switches provides a "closed switch" input signal to the stimulation device. This would occur, for example, when the individual is standing on the foot of the unimpaired leg. When the foot of the unimpaired leg is off the support surface, as, for example, during the swing phase of a gait, both switches would be open, and an "open switch" input signal would be provided to the stimulation device. The signals from switches 34, 36 are thus representative of gait events occurring in the unimpaired leg. When, and only when, either or both of foot switches 34, 36 are closed, electrical stimulation pulses are delivered on lead 38 to electrodes 42, 44 that effect dorsiflexion of the ankle of the impaired leg. When, and only when, both of the foot switches 34,36 are open, electrical stimulation pulses are delivered on lead 40 to electrodes 46, 48 that effect plantar flexion of the ankle of the impaired leg.

As shown in FIG. 3, the desired activation of the plantar flexor muscles in a leg for push off while walking occurs during a midstance phase of the gait for that leg and between the occurrence of a "toe off" event and a "contact" (heel strike) event of the other leg. At all other times, the dorsiflexor muscles are activated, i.e., during the loading, terminal stance and swing phases of the gait for the other leg. In the method and system of the present invention, these desired muscle activation patterns are achieved by using signals from heel and forefoot switches under the foot of the unimpaired leg to produce electrical stimulation delivered to dorsiflexor and plantar flexor muscles of the impaired leg.

The beneficial effects of the present invention when applied to a person with impaired walking ability manifested on one side (unilateral impairment) are demonstrated by the electromyographic data plotted in FIGS. 4A and 4B. The data in FIG. 4A show the activation levels during walking of dorsiflexor and plantar flexor muscles in one leg for an adult with normal walking ability. The data in FIG. 4B shown the activation levels during walking of dorsiflexor (anterior tibialis) and plantar flexor (gastrocnemius) muscles in an impaired leg of an adult with walking ability diminished due to stroke, while using the stimulation method and system of the present invention. As revealed by a comparison of the data in FIGS. 4A and 4B, the muscle activation patterns for a person with diminished walking ability, while using the method and system of the present invention, exhibit a remarkably good correlation to the muscle activation patterns for a person with normal walking ability.

Referring again to FIG. 2, the module 10 incorporates the electrical stimulator 12 and a motion detector and on/off controller 14 positioned between the stimulator and the electrodes 42, 44, 46, 48 that prevents electrical stimulation pulses from reaching the electrodes when the person using the system is inactive. As shown, the motion detector incorporates a power source 16, a sensor 18 that provides signals to a micro-controller 20 in response to movement/non-movement of the person. Switches 22, 23 operated by the micro-controller in response to the signals from the sensor determine the open/closed condition of the electrical paths between the electrical stimulator and the electrodes. The motion detector also incorporates a power switch and a bypass switch, as well as "on" and "off" indicator lights, respectively. When the patient is sensed to be walking, the motion detector enables transmission of the electrical stimulation pulses to the electrodes 42, 44, 46, 48. Conversely, when the patient is sensed to be not walking, the transmission of the pulses will be blocked. According to a setup scheme for the motion detector found to be suitable: the sensor is an accelerometer that senses accelerations occurring along each of two orthogonal axes; the pulses remain enabled for 1.5 seconds after walking has ceased and are then disabled; the pulses are enabled within 1 second after walking is detected. The power switch is operable to enable and remove power from all of the circuits in the controller 14. The bypass switch allows a technician to set up the intensity of the electrical stimulation, based on the therapeutic effect and comfort response, when the individual using the device is inactive.

The method and system of the present invention is also applicable to persons having bilateral impairment of their walking ability. As illustrated schematically in FIG. 5, an embodiment of the invention that may be used for this purpose employs a module 60 which, like the module 10 used in the unilateral embodiment, is configured to receive signals from switches placed under the heel and forepart, respectively, of the foot of one leg and provide electrical stimulation to at least two muscles of the other leg. As shown, input leads 30, 32 conduct signals to the module 60 from switches 34, 36 under the foot of the right leg. Output leads 38, 40 conduct electrical stimulation pulses from the module to electrodes 42, 44, 46, 48 positioned to apply the stimulation pulses to muscles of the left leg that contract in response to the electrical stimulation to effect dorsiflexion and plantar flexion of the ankle of the left leg. The module 60 is configured to also receive signals from another set of foot switches and provide electrical stimulation pulses to another set of electrodes. As shown, input leads 80, 82 conduct signals to the module 60 from switches 84, 86 under the foot of the left leg. Output leads 88, 90 conduct electrical stimulation pulses from the module to electrodes 92, 94, 96, 98 positioned to apply the stimulation pulses to muscles of the right leg that contract in response to the electrical stimulation to effect dorsiflexion and plantar flexion of the ankle of the right leg.

The module 60 may employ a bundle of two electrical stimulation devices like the electrical stimulation device 12 employed in the unilateral embodiment of the invention. In such a module, one of the electrical stimulation devices would have an input from foot switches 34, 36 and outputs to electrodes 42, 44, 46, 48; the other of the electrical stimulation devices would have an input from foot switches 84, 86 and outputs to electrodes 92, 94, 96, 98. Alternatively, the module 60 could employ a single electrical stimulation device configured to deliver electrical stimulation pulses on first and second pairs of output channels that are each triggered by an external switch. In this configuration, one pair of output channels, corresponding to leads 38, 40, would deliver electrical stimulation in the form of low voltage output pulses to electrodes 42, 44, 46, 48 in response to a first input via leads 30, 32 of signals from switches 34, 36. Similarly, the other pair of output channels, corresponding to leads 88, 90, would deliver electrical stimulation to electrodes 92, 94, 96, 98 in response to a second input via leads 80, 82 of signals from switches 84, 86.

In the bilateral embodiment of the invention, both pairs of foot switches would be connected in parallel between the leads providing inputs to the module 60. The motion detector and on/off controller 64, positioned between the electrical stimulator(s) and the electrodes applied to both legs, could be a modification of the motion detector and on/off controller 14 used with the unilateral embodiment of the invention. The controller 64 could, for example, be a modification of controller 14 wherein the micro-controller 20 operates four switches that cause the electrical paths between the electrical stimulator(s) and the electrodes to be open or closed. Like the controller 14, the controller 64 would enable the transmission of electrical stimulation pulses to the electrodes when the person is sensed to be walking and would block the transmission of the electrical stimulation pulses when the person is sensed to be not walking.

In the bilateral embodiment of the invention, gait event signals are developed from the switches positioned under the foot of each leg, and these gait event signals trigger the delivery of electrical stimulation to muscles of the other leg that effect dorsiflexion and plantar flexion of the ankle of the other leg. In both the unilateral and bilateral embodiments of the invention, the relationship between the delivery of electrical stimulation to a leg and the gait event signals derived from the other leg is the same.

Because of the relatively uncomplicated design of the equipment of the present invention, family members will be able to properly apply and take off the equipment each day. This will enable individuals with disabilities to wear the equipment for several hours each day, which will facilitate motor learning and re-training of the motor patterns for walking.

Modifications of the method and system of the present invention will likely occur to those who have had the benefit of the foregoing disclosure. For example, the signals from the foot switches to the module could be transmitted wirelessly instead of through electrical conductors. The module used in either or both of the unilateral and bilateral embodiments of the invention may incorporate, within a unitary housing, an electrical stimulator, a motion detector and on/off controller, a single power source for all of the powered units, and a single micro-controller providing logic controls for the electrical stimulator and the on/off controller.

What is claimed is:

1. A method of providing walking assistance and/or therapy to a person with impaired gait, the method comprising the steps of:
   sensing pressure between the heel of the foot of one leg and a support surface while walking;
   sensing pressure between the forepart of the foot of one leg and a support surface while walking;
   developing first gait event signals in response to the pressure sensed between the heel of the foot of one leg and a support surface while walking;
   developing second gait event signals in response to the pressure sensed between the forepart of the foot of the one leg and the support surface while walking;
   applying electrical stimulation to at least one muscle in the other leg that effects dorsiflexion of the ankle of the other leg only in response to at least one of the first and second gait event signals; and
   applying electrical stimulation to at least one muscle in the other leg that effects plantar flexion of the ankle of the other leg only when both of the first and second gait event signals are absent; wherein
   electrical stimulation is applied at all times while walking to one or the other of (1) the at least one muscle in the other leg that effects dorsiflexion of the ankle of the other leg and (2) the at least one muscle in the other leg that effects plantar flexion of the ankle of the other leg.

2. The method as recited in claim 1, wherein the first and second gait event signals are developed from electrical switches located under the heel and forepart, respectively, of the foot of the one leg.

3. The method as recited in claim 1, and further comprising the steps of:
sensing movement of the person;
developing an activity signal in response to the sensed movement of the person;
allowing the application of electrical stimulation in response to the activity signal; and
blocking the application of electrical stimulation when the activity signal is absent.

4. The method as recited in claim 3, wherein the activity signal is developed in response to movement of the person along each of two orthogonal axes.

5. A method for providing walking assistance and/or therapy to a person with impaired gait, the method comprising the steps of:
sensing pressure between the heel of the foot of each leg and a support surface while walking;
developing first gait event signals in response to the pressure sensed between the heel of the foot of each leg and a support surface while walking;
sensing pressure between the forepart of the foot of each leg and a support surface while walking;
developing second gait event signals in response to the pressure sensed between the forepart of the foot of each leg and the support surface while walking;
applying electrical stimulation to at least one muscle in each leg that effects dorsiflexion of the ankle of the leg only in response to at least one of the first and second gait event signals derived from the other leg; and
applying electrical stimulation to at least one muscle in each leg that effects plantar flexion of the ankle of the leg only when both of the first and second gait event signals derived from the other leg are absent; wherein
electrical stimulation is applied at all times while walking to the at least one muscle in each leg that effects dorsiflexion of the ankle or plantar flexion of the ankle.

6. The method as recited in claim 5, wherein the first and second gait event signals are developed from electrical switches located under the heel and forepart, respectively, of the foot of each leg.

7. The method as recited in claim 5, and further comprising the steps of:
sensing movement of the person;
developing an activity signal in response to the sensed movement of the person;
allowing the application of electrical stimulation in response to the activity signal; and
blocking the application of electrical stimulation when the activity signal is absent.

8. The method as recited in claim 7, wherein the activity signal is developed in response to movement of the person along each of two orthogonal axes.

9. A system for providing walking assistance and/or therapy to a person with impaired gait, the system comprising:
a first sensor for sensing pressure between the heel of the foot of one leg and a support surface while walking and developing a first gait event signal in response to the pressure sensed between the heel of the foot of one leg and a support surface while walking;
a second sensor for sensing pressure between the heel of the foot of one leg and a support surface while walking and developing a second gait event signal in response to the pressure sensed between the forepart of the foot of the one leg and the support surface while walking; and
at least one pair of first electrodes for applying electrical stimulation to at least one muscle in the other leg that effects dorsiflexion of the ankle of the other leg;
at least one pair of second electrodes for applying electrical stimulation to at least one muscle in the other leg that effects plantar flexion of the ankle of the other leg; and
an electrical stimulation device configured to receive the first and second gait event signals and provide an electrical stimulation output to the electrodes, the electrical stimulation device providing (1) an electrical stimulation output to the at least one pair of first electrodes in only response to the reception of at least one of the first and second gait event signals and (2) an electrical stimulation output to the at least one pair of second electrodes only when both of the first and second gait event signals are absent; wherein
an electrical stimulation output is applied at all times while walking to one or the other of (1) the at least one pair of first electrodes and (2) the at least one pair of second electrodes.

10. The system as recited in claim 9, wherein the first and second sensors are electrical switches adapted to be located under the heel and forepart, respectively, of the foot of the one leg.

11. The system as recited in claim 10, wherein
electrical conductors provide an input to the electrical stimulation device; and
the switches are connected in parallel electrically between the electrical conductors.

12. The system as recited in claim 9, and further comprising:
a third sensor for sensing activity of the person and developing an activity signal in response to the sensed activity of the person; and
a control device that (1) allows the electrical stimulation outputs in response to the activity signal and (2) blocks the electrical stimulation outputs when the activity signal is absent.

13. The system as recited in claim 12, wherein the third sensor is an accelerometer.

14. The system as recited in claim 13, wherein the accelerometer senses accelerations occurring along each of two orthogonal axes.

15. A system for providing walking assistance and/or therapy to a person with impaired gait, the system comprising:
first sensors for sensing pressure between the heel of the foot of each leg and a support surface while walking and developing first gait event signals in response to the pressure sensed between the heel of the foot of each leg and a support surface while walking;
second sensors for sensing pressure between the heel of the foot of each leg and a support surface while walking and developing second gait event signals in response to pressure sensed between the forepart of the foot of each leg and the support surface while walking;
at least one pair of first electrodes for applying electrical stimulation to at least one muscle in each leg that effects dorsiflexion of the ankle of the leg;
at least one pair of second electrodes for applying electrical stimulation to at least one muscle in each leg that effects plantar flexion of the ankle of the leg; and
an electrical stimulation device configured to receive the first and second gait event signals derived from each leg and provide an electrical stimulation output to the electrodes of the other legs, the electrical stimulation device providing (1) an electrical stimulation output to the at least one pair of first electrodes of each leg only in response to the reception of at least one of the first and second gait event signals derived from the other leg and (2) an electrical stimulation output to the at least one pair of second electrodes of each leg only when both of the first and second gait event signals derived from the other leg are absent; wherein for each leg, an electrical stimulation output is applied at all times while walking to one or the other of (1) the at least one pair of first electrodes and (2) the at least one pair of second electrodes.

16. The system as recited in claim 15, wherein the first and second sensors are electrical switches adapted to be located under the heel and forepart, respectively, of the foot of each leg.

17. The system as recited in claim 16, wherein the switches under the foot of one leg are connected in parallel electrically between electrical conductors providing an input to the electrical stimulation device, and the switches under the foot of the other leg are connected in parallel electrically between electrical conductors providing another input to the electrical stimulation device.

18. The system as recited in claim 15, and further comprising:

a third sensor for sensing activity of a person and for developing an activity signal in response to sensed activity of the person; and a control device that (1) allows the application of electrical stimulation in response to the activity signal and (2) blocks the application of electrical stimulation when the activity signal is absent.

19. The system as recited in claim 18, wherein the third sensor is an accelerometer.

20. The system as recited in claim 19, wherein the accelerometer senses accelerations occurring along each of two orthogonal axes.

* * * * *